United States Patent [19]

Christ et al.

[11] Patent Number: 5,147,397
[45] Date of Patent: Sep. 15, 1992

[54] INTRAOCULAR LENS AND METHOD FOR MAKING SAME

[75] Inventors: F. Richard Christ, Laguna Beach; David A. Fencil, Goleta; Patricia M. Knight, Laguna Niguel, all of Calif.

[73] Assignee: Allergan, Inc., Irvine, Calif.

[21] Appl. No.: 547,859

[22] Filed: Jul. 3, 1990

[51] Int. Cl.$^5$ ............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 3,776,829 | 12/1973 | Goan . | |
| 3,994,027 | 11/1976 | Jensen et al. | 623/6 |
| 4,025,965 | 5/1977 | Siegmund | 623/6 |
| 4,307,043 | 12/1981 | Chase et al. | 264/1.7 |
| 4,502,163 | 3/1985 | Graham | 623/6 |
| 4,615,702 | 10/1986 | Koziol et al. | 623/6 |
| 4,619,662 | 10/1986 | Juergens, Jr. | 623/6 |
| 4,662,882 | 5/1987 | Hoffer | 623/6 |
| 4,668,446 | 5/1987 | Kaplan et al. | 623/6 |
| 4,701,288 | 10/1987 | Cook et al. | 264/1.4 |
| 4,702,865 | 10/1987 | Koziol et al. | 264/17 |
| 4,718,905 | 1/1988 | Freeman | 623/6 |
| 4,737,322 | 4/1988 | Bruns et al. | 623/6 |
| 4,790,846 | 12/1988 | Christ et al. | 623/6 |
| 4,834,751 | 5/1989 | Knight et al. | 623/6 |
| 4,936,849 | 6/1990 | Knoll et al. | 623/6 |

FOREIGN PATENT DOCUMENTS 9004512 5/1990 PCT Int'l Appl. ............ 623/6

OTHER PUBLICATIONS

Cormia et al, "Use Plasmas To Re-engineer Your Advanced Materials", R&D Magazine, Jul. 1990.
Chawla, A. S., Use of Plasma Polymerization for Preparing Silicone-Coated Membranes for Possible Use in Blood Oxygenators, Artificial Organs vol. 3 No. 1, 1979, pp. 92-96.
Evans et al, Introduction of Functional Groups onto Carbon Electrodes via Treatment with Radio-Frequency Plasmas, Analytical Chemistry, vol. 51 No. 3, 1979, pp. 358-365.
Donnet et al, Plasma Treatment Effect on the Surface Energy of Carbon and Carbon Fibers, Carbon vol. 24, No. 6, pp. 757-770, 1986.

*Primary Examiner*—Randy C. Shay
*Attorney, Agent, or Firm*—Gordon L. Peterson; Frank J. Uxa, Jr.

[57] ABSTRACT

Disclosed is a method for producing an intraocular lens including an optic and at least one haptic. In one embodiment, the method comprises: exposing the lens bonding region of the haptic to a plasma at conditions effective to enhance the bondability of the lens bonding region to the optic; and bonding the exposed lens bonding region to an optic. The plasma exposed haptic may be coated with a material, e.g., to preserve the enhanced bondability property, prior to bonding the coated lens bonding portion to the optic. Intraocular lenses having enhanced haptic-optic bonding are also disclosed.

17 Claims, 2 Drawing Sheets

INTRAOCULAR LENS AND METHOD FOR MAKING SAME

BACKGROUND OF THE INVENTION

The present invention relates to an improved intraocular lens. More particularly, the present invention relates to soft-type intraocular lens having improved bonding strength between the haptic or haptics and the optic of the lens.

The use of intraocular lenses (IOLs) to improve vision and/or to replace damaged or diseased natural lenses in human eyes, particularly natural lenses impaired by cataracts, has obtained wide acceptance. Accordingly, a variety of IOLs has been developed for surgical implantation in the posterior or anterior chambers of the eye according to a patient's needs.

Known IOLs comprise an optical lens portion or optic which includes an optical zone, and one or more, preferably two, supporting structures, called fixation members or haptics, for contacting eye tissue to fix or hold the IOL in the proper position after implantation. The optic may comprise a soft, resilient material, such as any of a variety of flexible elastomers, or a relatively hard or rigid material such as, for example, polymethylmethacrylate (PMMA). The haptics typically comprise a filament constructed of resilient metal or polymeric substance, such as PMMA or polypropylene.

Each of the filament haptics is preferably flexible to reduce trauma to sensitive eye structures and to be yielding during insertion of the IOL. In addition, filament haptics generally have a memory retaining capability, e.g., springiness, so that after implantation of an associated IOL, the filament haptics automatically tend to return to their normal orientations.

As an alternative to filament haptics, some IOLs are provided with footplate-type haptics. These footplates generally extend radially outwardly from the optic (in the plane of the optic) and terminate in rounded or blunted ends configured for placement in an eye chamber. The materials for such footplates have included soft materials, for example 2-hydroxyethyl methacrylate or silicone. However, footplate-type haptics are attended by disadvantages, such as the addition of extra material weight to the IOL and reduced flexibility as compared to filament haptics leading to poor fixation and consequent migration or dislocation of the IOL.

Although the filament haptics are preferred over the footplate-type haptics for several reasons, certain difficulties remain. For example, filament haptics and soft or deformable optics tend to be formed from dissimilar materials which do not ordinarily chemically bond together. As a result, filament haptics have been designed having a variety of attachment end configurations or structures, e.g., anchor structures for providing a physical interlock between the haptic and optic. Polypropylene haptics, for example, have heretofore been secured into silicone polymer-based optics by means of a mechanical lock. This lock may comprise a small loop or other anchor formed at the attachment end of the haptic through and/or around which the silicone-based optic precursor material is poured or molded and then cured. Christ et al U.S. Pat. No. 4,790,846 discloses the molding of an optic around a haptic having a small loop or other anchor to effect a secure haptic connection.

Christ et al U.S. Pat. No. 4,790,846 further discloses a method for making an IOL in which a region of an elongated filament haptic has a different configuration, e.g., a bulbous enlargement, which cooperates with the optic of the IOL to form a mechanical interlock between this different configuration and the optic and to attach to the optic. If desired, the bulbous enlargement may have its outer surface roughened to improve adhesion of the material of the optic.

Koziol, et al U.S. Pat. Nos. 4,615,702 and 4,702,865 disclose a one-piece haptic structure which comprises an annular loop portion for surrounding the optical pathway or zone through the optic, and having a pair of mounting arms extending radially outwardly from the loop. The loop is embedded within the optic during molding and polymerization of the optic to provide a mechanical interfit. However, the loop can be aesthetically displeasing, and can interfere with peripheral sight through the optic. Also, due to the lack of chemical interaction between the haptic and the optic, gaps can form at the haptic-optic interface which further impair the optical integrity of the optic.

Kaplan et al U.S. Pat. No. 4,668,446 discloses an alternative method of attaching haptics to the optic of an IOL wherein an enlarged attachment end of the haptic is secured in the optic. This method involves an ethanol induced swelling of a bore hole in the optic, insertion of the enlarged end of the haptic into this bore hole, and removal of the ethanol to shrink the bore hole around the enlarged end of the haptic, thereby producing a mechanical anchoring.

Freeman U.S. Pat. No. 4,718,905 discloses an IOL including an optic composed of PMMA and haptics fashioned from polypropylene strand material. Each haptic strand is coated, using ion beam implantation, with a biocompatible protective covering material to protect it from the bioerodable effects of ocular tissue. This patent does not teach, or even suggest, enhanced haptic-optic bonding. Also, there is no teaching that the haptic is subjected to ion beam implantation prior to being secured to the optic.

Bruns et al U.S. Pat. No. 4,737,322 discloses an IOL including haptics with anchoring struts which are located in the optic and surround or partially surround the center of the optical zone portion of the optic. These struts provide sufficient anchoring of the haptic in the optic to withstand a tensile pull force of from 50 to 115 grams.

Notwithstanding these known structures and methods, there remains a need for a method of efficiently and effectively securing a haptic to the optic of an IOL, preferably without the use of mechanical interlocking structures, so that the strength of the haptic-optic bond is sufficient to resist detachment of the haptic under normal implantation and wear conditions.

The use of gas plasmas to activate and/or add functional groups to surfaces or fibers is well known. For example, see: "Plasma Treatment Effect in the Surface Energy of Carbon and Carbon Fibers", J. B. Donnet, et al, Carbon, Vol. 24, No. 6 pp 757–770 (1986); and "Introduction of Functional Groups Onto Carbon Electrode Via Treatment With Radio-Frequency Plasma", J. F. Evans, et al, Analytical Chemistry, Vol. 51, No. 3, pp 358–365 (1979). Further, Goan U.S. Pat. No. 3,776,829 discloses reacting carbon fibers with ammonia plasma to form amino groups on the fiber surfaces. The amine groups act as cross linking agents for an epoxy resin matrix in the preparation of sized fibers, preimpregnated tapes, and compositions containing the fibers. Heretofore, however, the known prior art has not disclosed or suggested the use of gas plasmas in the manufacture of IOLs.

SUMMARY OF THE INVENTION

New intraocular lenses and methods for making same have been discovered. The present IOLs have substantial haptic-optic bond strength so as to resist detachment of the haptic from the optic during normal surgical implantation and/or use. Such substantial haptic-optic bond strength is preferably achieved using haptics which have no enlarged structures, i.e., anchoring structures, designed to mechanically lock the haptic to the optic. The haptics are more preferably of the filament type in which a portion of the filament is bonded into the optic. Such relatively simple haptics are effective to fix the position of the IOL in the eye, while reducing, or even eliminating, interference with the optical field or zone of the optic. The present enhanced haptic-optic bond strength is particularly useful with optics constructed of soft, resilient, deformable materials which can be folded or rolled for insertion through a small incision into the eye.

In one broad aspect of the present invention, a method for securing at least one haptic to an optic is provided. This method comprises exposing the lens bonding region of the haptic to a plasma, preferably an activated gas plasma, and bonding the plasma-exposed lens bonding region of the haptic to an optic. More preferably, the plasma is generated from one or more of oxygen, nitrogen and argon gases. The optic is preferably deformable, and more preferably comprises one or more flexible polymers, such as certain flexible silicone polymers. The haptic preferably comprises a resilient material selected from polymeric materials, such as polypropylene, polyimide and PMMA, and metals, and more preferably comprises polypropylene.

The haptic-optic bonding step in one embodiment of the invention is accomplished by positioning the plasma-exposed lens bonding region of the haptic within a mold cavity structured for forming the optic of an IOL, and introducing optic precursor material into the mold cavity in contact with the plasma-exposed lens bonding region of the haptic. The optic precursor material is converted into the optic having the lens bonding region of the haptic bonded thereto.

The bonding step may alternatively be accomplished by coating the plasma-exposed lens bonding region of the haptic with a bondable material, and bonding this bondable material to the optic. This bondable material can be bonded to the optic, for example, either by molding optic precursor material with this bondable material in contact with, preferably included in, the optic precursor material, or by pacing this bondable material into a recess, e.g., channel, in a previously formed optic and bonding this bondable material and the material of the optic. In accordance with another aspect of the present invention, there is provided an intraocular lens produced in accordance with the methods disclosed herein.

In particular, an intraocular lens is provided which includes an optic, and at least one haptic, and preferably two haptics, having a lens bonding region which is bonded to, and preferably extends within, the optic. The lens bonding region is exposed to a plasma prior to being bonded to the optic. The bond strength between the haptic or haptics and the optic is increased, e.g., relative to a substantially identical IOL including a haptic with a lens bonding region which is not exposed to such a plasma, as a result of such plasma exposure.

In an additional aspect of the invention, an intraocular lens including an optic and at least one haptic is provided. The haptic has a lens bonding region with no anchor structures. This lens bonding region is bonded to, and preferably extends within the optic. The lens bonding region has a chemical composition different from that of the optic. The pull force required to separate the haptic from the optic is at least about 80 grams, preferably at least about 100 grams.

In accordance with a still further aspect of the present invention, there is provided a haptic assembly. This assembly comprises a haptic having a lens bonding region; and a material, e.g., a coating material, located on at least a portion of the lens bonding region. The lens bonding region is exposed in the presence of a plasma prior to being associated, e.g, coated, with the material. The bond strength between the haptic and the material is increased, e.g., relative to a substantially identical haptic assembly in which the lens bonding region is not exposed to such a plasma, as a result of such plasma exposure.

These and other aspects of the present invention are set forth in the following detailed description, examples and claims, particularly when considered in conjunction with the accompanying drawings in which like parts bear like reference numerals.

DETAILED DESCRIPTION OF THE INVENTION

Figure 1:
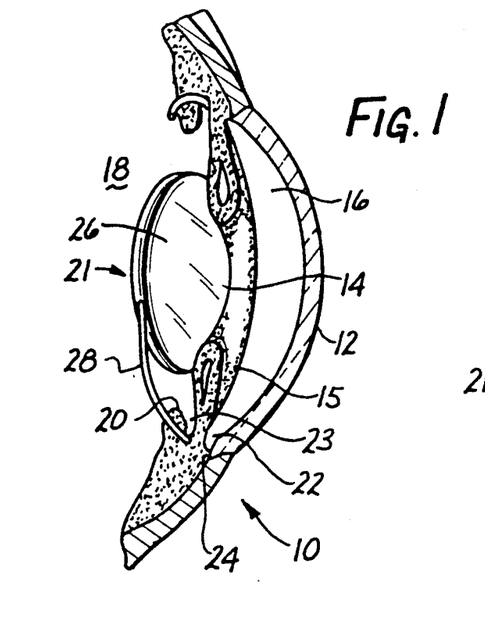
FIG. 1 is a simplified representation of the physiology of the human eye.

Referring to FIG. 1, there is depicted the in vivo placement into an eye 10 of an IOL 21 according to the present invention, in which lens bonding regions of the haptics have been exposed to plasma to provide enhanced bondability and bond strength to the associated optic, as more particularly described below.

The cornea 12 serves as a refracting medium in addition to its function as the anterior wall of the eye 10. The pupil 14 and the iris 15 of variable aperture are located behind the cornea 12 and divide the eye 10 into an anterior chamber 16 and a posterior chamber 18. The natural crystalline lens (not illustrated) is connected by zonular fibers to a peripheral muscle about the lens known as the ciliary muscle 20.

The surgical implantation of IOL 21 is accomplished by an incision in the eye 10, removal of the diseased or damaged natural lens (if applicable) and insertion of the IOL into the eye. The optic 26 of IOL 21 includes a centrally located optical zone and may be configured for implantation into a specific one or either of the anterior or posterior chambers 16 or 18. The haptics 28 of IOL 21 extend radially outwardly in the general plane of the optic 26.

A peripheral limit of anterior chamber angle 22 exists between the base of the iris 15 and a scleral spur, which serves as a support location for IOL 21 implanted within the anterior chamber 16 of the eye 10. A peripheral zone 23 also exists within the posterior chamber 18 between the ciliary muscle 20 and the base of the iris 15, which base is known as the ciliary sulcus 24. This peripheral zone 23 serves as a mounting location for IOL 21 within the posterior chamber 18. Referring to FIG. 1, IOL 21 is shown positioned in the posterior chamber 18 and is supported by the haptics 28 bearing upon the ciliary sulcus 24.

Figure 2:
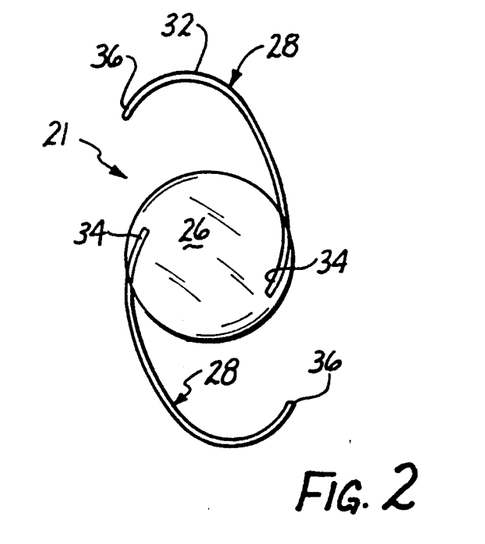
FIG. 2 is a plan view of an IOL in accordance with the present invention.
Figure 3:
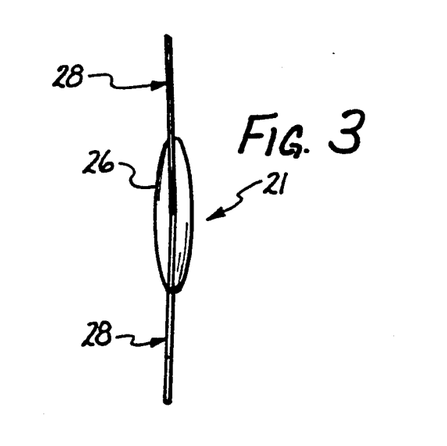
FIG. 3 is a side view of the IOL of FIG. 2.

Referring to FIGS. 2 and 3, IOL 21 is illustrated as including a pair of radially outwardly extending haptics 28 secured to optic 26. Each haptic 28 has a substantially uniform cross-section throughout its length and is shown provided with a smoothly curved region 32, intermediate a lens bonding region 34 and a free end region 36. Although the illustrated embodiment is provided with two opposing haptics 28, it is understood that an IOL having only one haptic or more than two haptics bonded to the optic by the method disclosed herein is considered within the scope of the invention.

Typically, each haptic 28 comprises a flexible member comprising metal or, preferably, polymeric material, and having a substantially circular cross-section, although alternative cross-sectional configurations may be substituted, if desired. The haptics 28 are relatively thin and flexible, while at the same time being sufficiently strong to provide support for IOL 21 in eye 10. The haptics 28 may comprise any of a variety of materials which exhibit sufficient supporting strength and resilience, and which are substantially biologically inert in the intended in vivo environment. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitonal, and the like. More preferably, the haptics 28 comprise a polymeric material, in particular selected from polypropylene, PMMA and polyimides, and especially polypropylene. The haptics can be produced using conventional and well known forming techniques. For example, the preferred polymeric haptics can be formed in accordance with known thermoplastic polymer forming techniques, such as by injection molding or by extrusion.

The lens bonding regions 34 of the haptics 28, which, as described herein, are secured to optic, may be provided with any of a variety of configurations, such as an anchoring loop, an anchoring "T", or other anchor structure, to provide a mechanical interlock with the optic, such as has been done in the prior art. However, although such haptic anchor structures contribute to the integrity of the bond between the haptic and the optic, the method of the present invention enables the use of simpler and less expensive haptics having a lens bonding region with no anchor structure, as illustrated in FIG. 2, while still achieving a haptic to optic bond of sufficient strength to prevent detachment of the haptic from the optic during handling, implantation and wear.

The present invention enables enhanced bonding between dissimilar haptic and optic materials, such as between the preferred polypropylene haptics and the preferred silicone polymer-containing optic. The provision of an enhanced bond between haptics 28 and optic 26 also reduces the formation of gaps at the interface of the haptics 28 and optic 26 which tend to reduce the strength of the haptic-optic bond.

In accordance with one embodiment of the present invention, enhanced bondability between the haptics 28 and the optic 26 is achieved by treating appropriate surface regions of the haptics prior to bonding the haptics to the optic. Although the surface of the entire length of each haptic can be treated in accordance with the method disclosed herein, preferably only the surface of such haptic which is to be in contact with the optic 26, i.e., the lens bonding region 34, is treated. Thus, for example, only the proximal-most about 2 to about 3 or about 4 mm of each haptic 28 is preferably treated.

The preferred mode of treating the lens bonding region 34 of each haptic 28 is to expose this region to a plasma. The plasma may have its origin from any of a variety of materials, preferably gases, in particular gases such as oxygen, nitrogen or argon. More preferably, an oxygen plasma is used.

Methods for generating a plasma are well known in the art, and need not be extensively described here. In general, the haptic 28 is placed in a chamber containing the plasma. This may be accomplished by inserting only the lens bonding region 34 through an opening in the wall of the chamber, so that only the desired portion of haptic 28 is exposed to the plasma. Alternatively, the entire haptic 28 can be exposed to the plasma, preferably after having masked all but the lens bonding region 34 of the haptic.

Masking is preferably accomplished by dipping, spraying or encasing the haptic 28, except the lens bonding region 34, in a plasma resistant material, such as cured silicone or other polymer which resists, and preferably substantially prevents, penetration of the plasma to the surface of the haptic lying beneath the masking material, and which can later be removed without damage to the haptic.

In accordance with one embodiment of the method of the present invention, radio frequency, inductively-coupled plasma is produced in a plasma chamber by charging the chamber with gas, e.g., oxygen, preferably at a sub-atmospheric pressure of about 0.01 torr (mm Hg) or greater, more preferably at a pressure in the range of about 0.05 torr to about 0.3 torr. The preferred output power is in the range of about 10 watts to about 500 watts, more preferably about 30 watts to about 120 watts, and still more preferably about 70 watts to about 90 watts.

The haptic 28 is preferably exposed to the plasma for a period of time in the range of about 1 minute to about 60 minutes, more preferably about 5 minutes to about 60 minutes and still more preferably about 15 minutes to about 30 minutes. However, the specific gas, exposure time, power, and/or other parameters may be varied depending upon the equipment and the particular haptic and optic materials involved, and can be readily optimized based upon the disclosure herein using routine experimentation.

Although the present invention is not limited to any particular mechanism, and without limiting the present invention to any particular theory of operation, the present methodology is believed to cause a physical and chemical modification or alteration of the exposed regions of the haptic, which in turn results in enhanced bonding between the plasma exposed regions of the haptic and the optic. The enhanced ability of chemical functionalities at the plasma exposed haptic surfaces to react with active groups, for example, hydride or vinyl groups, in the optic precursor material may provide for at least a portion of the enhanced bondability and bonding of the present invention.

In any event, lens bonding region 34 of haptic 28 is exposed to a plasma at conditions effective to enhance, e.g., relative to a substantially identical haptic having a lens bonding region which is not so exposed to a plasma, the bondability of the lens bonding region to optic 26.

After plasma exposure, the haptic 28 is removed from the plasma chamber and bonded to the optic 26. The treated haptic 28 can be bonded either to the optic 26 directly, or to an intermediate coating material which itself is bondable to the optic.

Bonding of the plasma-exposed haptic 28 directly to the optic 26 is preferably accomplished within about 48 hours after the plasma-exposure is completed, more preferably within about 24 hours after the plasma-exposure is completed, and still more preferably within about 3 hours, in particular about 30 minutes to about 3 hours, after the plasma-exposure is completed.

Figure 4:
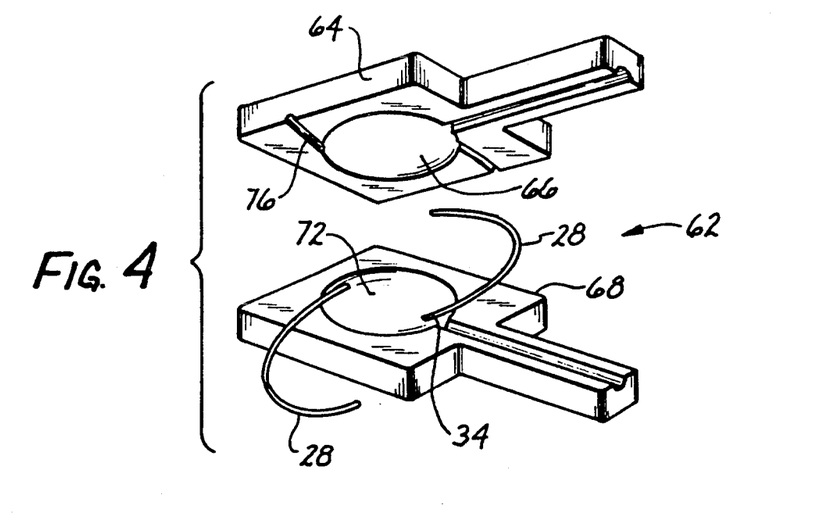
FIG. 4 is a perspective representation of a mold for forming an optic in accordance with the present invention.

Bonding of the haptic 28 directly to the optic 26 is preferably accomplished in a mold 62, such as that illustrated in FIG. 4. The mold 62 comprises an upper plate 64 with an upper concave cavity 66 and a lower plate 68 with a lower concave cavity 72. The upper plate 64 and/or lower plate 68 of the mold 62 are movable relatively toward and away from each other in order to permit insertion of the lens bonding regions 34 of haptics 28 therein, introduction of liquid precursor material for forming the optic 26, and removal of the combined optic and haptics (i.e. IOL 21) once the optic is fully cured.

In the illustrated embodiment, the lower plate 68 and upper plate 64 of the mold 62 are each provided with a pair of grooves 76 into and through which the haptics 28 are inserted into the combination of upper concave cavity 66 and lower concave cavity 72.

Thus, in forming the IOL 21 in accordance with one embodiment of the invention, the mold plates 64 and 68 are initially separated, and the plasma-exposed haptics 28 are positioned in the grooves 76 so that the lens bonding regions 34 are located inside of the combination of upper concave cavity 66 and lower concave cavity 72 when the mold plates 64 and 68 are brought together. Next, a pre-polymer or monomer material, preferably in a viscous liquid form, is introduced into the upper concave cavity 66 and the lower concave cavity 72. Preferably, the pre-polymer or monomer material is introduced in a volume somewhat greater than the sum of the volumes of the two cavities 66 and 72, as is well known in the art, so that it is assured that the combined cavity is completely filled, the excess material being discharged. The mold plates 64 and 68 are then brought together to form the combination of upper concave cavity 66 and lower concave cavity 72, and the pre-polymer or monomer material in this combined cavity is converted into the optic 26, such as by heat curing.

The optic 26 typically comprises an optically suitable and biologically compatible polymer, many of which are known in the art. For example, a two-part silicone formulation may be introduced into the mold cavity at a weight ratio of about 1:1, as is known to one of skill in the art. Part A typically includes a catalyst and a base polymer. Part B typically includes a cross-linker and the same base polymer. The base polymer is preferably synthesized from siloxanes, in particular cyclic siloxanes. Preferably, the optic 26 comprises a polymer which is a platinum-catalyzed, vinyl/hydride addition cured poly (organo siloxane), more preferably incorporating a covalently bonded vinyl-functional benzotriazole for ultraviolet blocking. A particularly useful optic composition includes a silicone-based polymer which is reinforced, for example, with a suitable resin and/or silica.

The optic 26 may comprise materials such as hydrogel-forming polymers, polyphosphazenes, polyurethanes and polyacrylates, as well as silicone polymers, and mixtures thereof, e.g., such as are known in the art. The enhanced haptic-optic bond strength of the present invention is particularly advantageous when the optic 26 is constructed of soft, resilient, deformable materials. Rigid optic materials, such as polycarbonates, polysulphones and PMMA, may also be used. In all cases, the particular material should produce an optically clear optic and exhibit biocompatibility in the environment of the eye. Selection parameters for suitable intraocular lens materials are well known to one of skill in the art.

Following introduction into the mold 62, the pre-polymer or monomer material is converted, such as by heat promoted polymerization and/or curing, into a solid or a semi-solid polymer. The conversion may be initiated by any appropriate initiator and/or promotor suitable for the particular pre-polymer or monomer material employed. When the optic precursor material is initially introduced into the mold 62, it surrounds and contacts the plasma-exposed lens bonding regions 34 of haptics 28 so that the lens bonding regions of the haptics are bonded into the optic after conversion of the optic precursor material.

Alternatively, rather than introducing the pre-polymer or monomer material into an open mold 62 and then closing the mold, the mold can be closed after insertion of the plasma-exposed lens bonding regions 34 of haptics 28 and the pre-polymer or monomer material can then be injected into the combined cavities 66 and 72 under pressure via a suitable input port. Conversion of the pre-polymer or monomer material, as described above, is thereafter accomplished.

In accordance with another embodiment of the method of the present invention, slender inert rods or wires (not illustrated) are introduced into the mold grooves 76 in place of the plasma-exposed lens bonding regions 34 of haptics 28. Preferably, such rods or wires have substantially the same cross-sectional configuration as the intended haptics, and are inserted into the mold 62 to a depth which is approximately equal to the length of the plasma-exposed lens bonding regions 34 of the haptics 28. In this embodiment, the optic 26 is formed, as previously mentioned, around the portions of the rods or wires extending into the combined cavities 66 and 72. Afterwards the rods or wires are pulled from the optic 26 to produce an optic containing cylindrical recesses extending into the optic for thereafter receiving the plasma-exposed lens bonding regions 34 of haptics 28.

As a further alternative, the optic 26 may be molded without insertion into the mold of either the haptics 28 or the rods or wires, thereby producing an optic without haptics or recesses. The optic 26 is subsequently provided with one or more recesses for receiving one or more plasma-exposed haptics 28. These recesses may be produced in a variety of ways known to one of skill in the art.

Either of the two immediately preceding methods of the present invention results in an optic 26 having haptic-receiving recesses therein. The plasma-exposed haptics 28 may thereafter be secured into the recesses by a variety of methods, such as by introducing a bonding substance into the recesses within the optic 26, prior to the introduction of the lens bonding regions of the haptics, for bonding the haptics in the optic.

Substances useful to bond the plasma-exposed haptics 28 to the optic 26 include polymerizable monomeric or polymeric substances which can be bonded to both the plasma-exposed lens bonding regions 34 of the haptics and the optic. In one embodiment, a bonding substance capable of forming a polymeric material having substantially the same or a similar chemical composition as the polymer material of the optic 26 is used. For example, silicone-based bonding substances may be used which, when polymerized, are substantially the same as or similar to the preferred flexible polymer of the optic 26. Either as an alternative to, or in addition to, the use of a separate bonding substance, the material of the optic 26 may be only partially cured at the time of insertion of the plasma-exposed haptics 28. The material is thereafter completely cured, such as by the addition of heat, to form a bond between the optic 26 and the haptics 28.

The bondability of the plasma-exposed lens bonding regions 34 of the haptics 28 to the optic 26 is dependent on the amount of time which elapses from completion of the plasma exposure to the haptic bonding operation. For manufacturing reasons, it may not always be practical to bond the plasma-exposed haptics 28 to the optic 26 within an advantageous time period after the plasma treatment. Thus, it may be desirable to prolong the bondability of the plasma-exposed haptic.

For this purpose, the plasma-exposed lens bonding regions 34 of the haptics 28 may be provided with an appropriate coating material which is capable of bonding to both the haptics and to the optic 26. Provision of such a coating within the preferred time periods following plasma exposure specified above enables a secure bond to form between the haptics 28 and the coating material. The coating on the plasma-exposed haptic 28 is then bonded to the optic 26, e.g., using one of the techniques disclosed herein for bonding the plasma-exposed haptics to the optic. As a result of using this coating technique, the time from completion of the plasma-exposure is much reduced as a factor in the timing of the haptic-optic bonding operation. The coating material may be a different material than either one or both of the haptics 28 and the optic 26. In a particularly useful embodiment, the coating material, in its fully polymerized form, has substantially the same or a similar chemical composition as the polymer material of the optic 26.

Figure 6:
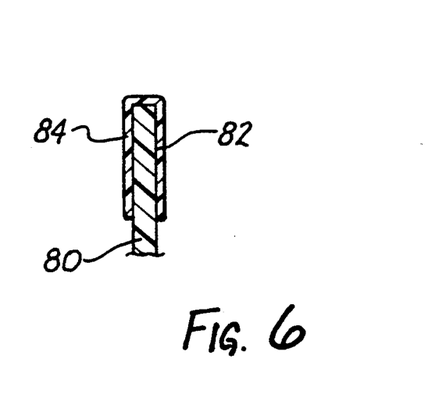
FIG. 6 is a partial cross-sectional view of a haptic assembly of the present invention.

In a specific embodiment illustrated in FIG. 6, a polypropylene or PMMA haptic 80 is coated with an uncured or partially cured silicone-based polymer within about 30 minutes to about 3 hours following exposing the lens bonding region 82 of the haptic to an activated gas plasma in accordance with the present invention. The coating material may be applied by known spraying or dipping operations and have a preferred thickness in the range of about 100 microns to about 1,000 microns, more preferably about 100 microns to about 500 microns. Preferably, the coating material is substantially uniform in thickness around the circumference of the lens bonding region 82 of the haptic 80. The plasma-exposed lens bonding region 82 may then be bonded to the coating material, e.g., using heat to cure the coating material, and form a coating 84 on the lens bonding region of haptic 80.

The coated, plasma exposed haptic 80 may thereafter be bonded to the optic 26, e.g., using the methods described above for uncoated plasma-exposed haptics. For example, a haptic 80 having a silicone-based polymer coating 84 on the lens bonding region 82 thereof, can be inserted into a mold in which a silicone polymer-based optic 26 is to be formed. Cross linking between the haptic coating and the optic 26 can be optimized by the addition of suitable cross linking enhancers, such as are well known in the art, and/or by leaving the silicone coating less than completely cured prior to the optic forming operation.

Haptics 28 which have been coated as described within the appropriate time period following plasma-exposure have been found to provide enhanced haptic-optic bonding, e.g., relative to a substantially identical coated haptic which is not exposed to such plasma. The useful shelf life of the coated haptics 28 is dependent on the bonding characteristics of the coating to the optic 26.

The following non-limiting examples illustrate certain aspects of the present invention.

The optic-like elements referred to in the Examples were substantially right circular cylindrical in shape, having a diameter of 10 mm, and a height of 1 mm. These optic-like elements substantially simulate the configuration of an optic in an IOL so that the results, e.g., amounts of pull force required to separate the haptics from the optic-like elements, obtained with such optic-like elements are correlatable to pull force results which would be using real IOL optics.

EXAMPLE 1

Four (4) groups of test specimens were prepared. Each of the test specimens included a silicone polymer-based optic-like element, and two haptics.

Each of the optic-like elements had the same chemical composition, a resin reinforced platinum-catalyzed, vinyl/hydride addition-cured polyorganosiloxane polymer. A vinyl functional benzotriaizole was covalently bonded into this polymer to provide for ultraviolet light absorbance. The refraction index of this polymer was about 1.412.

Each of the haptics was made of polypropylene. The anchor loop, if any, of the haptic was positioned so that the center of the loop was about 2 mm into the optic-like element. Each of the haptics without an anchor loop had a substantially uniform cross-sectional area and was positioned so that the end of the haptic in the optic extended about 2 mm into the optic-like element.

The first group of test specimens, i.e., Group 1, were prepared using haptics with anchor loops. The lens bonding regions of these haptics which were to be included in the optic-like element were first exposed to an oxygen plasma at 80 watts power, and a pressure of 0.1 torr for a duration of about 30 minutes. The plasma generator used was that sold by RF Plasma Products, Inc. under the trademark RF-S. The plasma exposed lens bonding regions of the haptics were thereafter bonded into the optic-like element, by appropriately positioning the plasma exposed lens bonding region of the haptic in the precursor of the silicone polymer and conventionally curing this precursor. This curing took place within about three (3) hours after the completion of the plasma treatment.

The second group of test specimens, i.e., Group 2, were prepared as were the Group 1 test specimens except that the haptics used included no anchor loops.

The third group of test specimens, i.e., Group 3, were prepared as were the Group 1 test specimens except that the haptics were not exposed to any plasma.

The fourth group of test specimens, i.e., Group 4, were prepared as were the Group 2 test specimens except that the haptics were not exposed to any plasma.

After the test specimens had been prepared, each of them was tested as follows. Using an Instron Model 1122 tensile tester, the haptics were pulled from the optics-like elements, and the pull force required to achieve this separation was recorded.

Results of these tests were as follows:

|  | Anchor Loop | Plasma Treatment | Pull Strength | Number of Haptics in Group |
| --- | --- | --- | --- | --- |
| Group 1 | Yes | Yes | 144 ± 40 g | 33 |
| Group 2 | No | Yes | 112 ± 34 g | 33 |
| Group 3 | Yes | No | 53 ± 9 g | 26 |
| Group 4 | No | No | <40 g | 10 |

These data demonstrate the significantly superior strength of the haptic-optic bond which results from the plasma exposing step of the present invention. For haptics without anchor loops, for example, the mean pull force went from less than 40 grams with untreated haptics (Group 4) to 122±34 grams with plasma-treated haptics (Group 2). A significant improvement in the pull strength was also demonstrated for plasma-treated haptics with anchor loops (Group 1) over untreated haptics having anchor loops (Group 3). In addition, comparing Groups 2 and 3, the present plasma exposing step is more effective than anchor loops in increasing the strength of the haptic-optic bond. This is of substantial importance since it is advantageous, e.g., to reduce manufacturing complexity and to minimize interference with the optical zone of the optic, to employ haptics with no anchor means, e.g., anchor loops. Thus, the present invention preferably enables production of an intraocular lens including no anchor means having a haptic pull force of at least about 80 grams, and more preferably at least about 100 grams.

EXAMPLE 2

Five (5) groups of polypropylene haptics without anchor loops were treated by exposure of 1, 5, 15, 30 and 60 minute durations, respectively, to an oxygen plasma at 80 watts power and a pressure of 0.1 torr. Each group included five (5) haptics. Within three (3) hours after completion of the plasma treatment, each of the treated haptics was bonded into a silicone polymer-based optic-like element as described in Example 1. Following such bonding, the haptics were pulled from the optic-like elements by an Instron Model 1122 tensile tester and the pull force required to achieve this separation was recorded.

Results of these tests were as follows:

|  | Plasma Exposure Time (Minutes) | Mean Pull Force (gm) |
| --- | --- | --- |
| Group 1 | 1 | 4.3 ± 2.7 |
| Group 2 | 5 | 65.6 ± 22.5 |
| Group 3 | 15 | 99.1 ± 15.7 |
| Group 4 | 30 | 104.9 ± 23.5 |
| Group 5 | 60 | 98.2 ± 19.2 |

Figure 5:
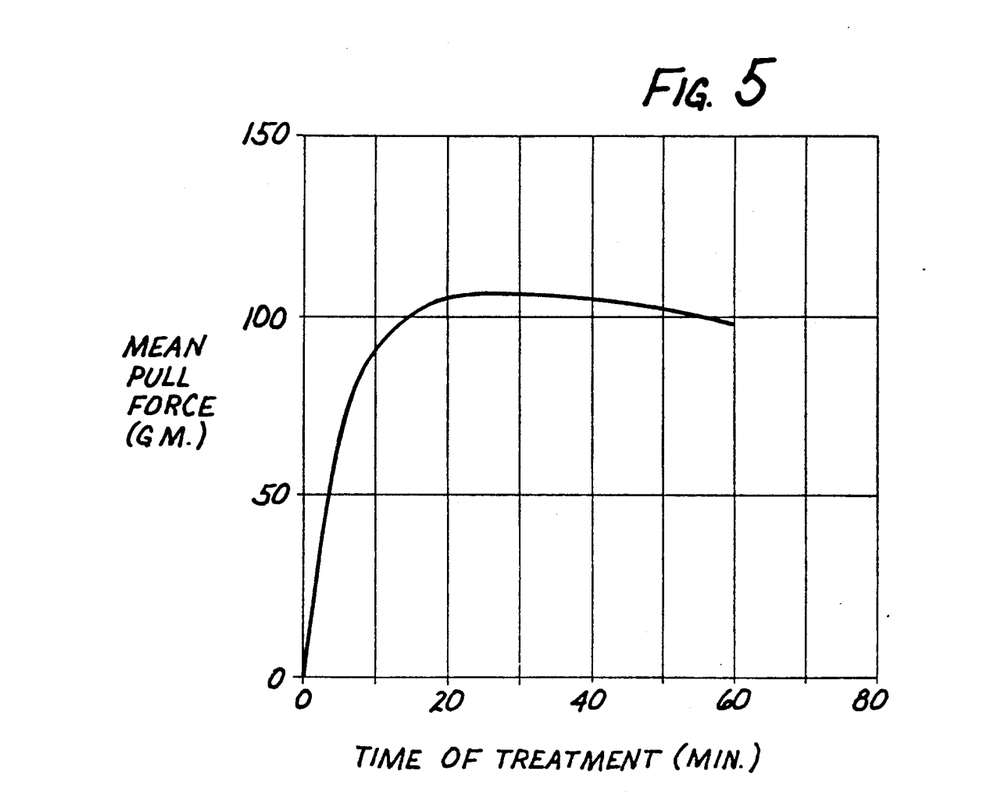
FIG. 5 is a graph of mean pull force vs. plasma exposure time for plasma-exposed polypropylene haptics molded into silicone polymer-based optics in accordance with the present invention.

These data are plotted in graphic form in FIG. 5. These results indicate that plasma exposure time has an effect on the pull strength which appears to reach a relative maximum for exposure times within the range of about 15 minutes to about one (1) hour, and in particular about 30 minutes.

EXAMPLE 3

Four (4) groups of polypropylene haptics without anchor loops were treated by exposure to a oxygen plasma for 15 minutes at power levels of 30, 50, 80 and 100 watts, respectively. The pressure in each of these plasma exposures was 0.1 torr. Each group included five (5) haptics. Within three (3) hours after completion of the plasma treatment, each of the treated haptics was bonded into a silicone polymer-based optic-like element as described in Example 1. Following such bonding, the haptics were pulled from the optic-like elements by an Instron Model 1122 tensile tester and the pull force required to achieve this separation was recorded.

Results of these tests were as follows:

|  | Power (Watts) | Mean Pull Force (gm) |
| --- | --- | --- |
| Group 1 | 30 | 87.3 ± 27.1 |
| Group 2 | 50 | 92.4 ± 9.6 |
| Group 3 | 80 | 114.4 ± 32.3 |
| Group 4 | 100 | 105.0 ± 12.4 |

These results indicate that the plasma power level has an effect on pull strength, and that a particularly useful power level is within the range of about 50 watts to about 100 watts.

EXAMPLE 4

Three (3) groups of five (5) polypropylene haptics without anchor loops were treated by exposure to a gas plasma. The gas used to plasma treat each group of haptics was different, as indicated below. Each of the plasma treatments was for 15 minutes at a power level of 80 watts. The pressure in each of the plasma treatments was 0.1 torr. Within three (3) hours after completion of the plasma treatment, each of the treated haptics was bonded into a silicone polymer-based optic-like element as described in Example 1. Following such bonding, the haptics were pulled from the optic-like element by a Instron Model 1122 tensile tester and the pull force required to achieve this separation was recorded.

Results of these tests were as follows:

|  | Plasma Gas | Mean Pull Force (gm) |
| --- | --- | --- |
| Group 1 | Oxygen | 126.4 ± 16.9 |
| Group 2 | Nitrogen | 89.4 ± 17.6 |
| Group 3 | Argon | 87.8 ± 26.6 |

These results indicate that the strength of the haptic-optic bond varies as a function of the plasma gas, and that of the gases investigated oxygen provides the greatest pull strength.

EXAMPLE 5

Six (6) groups of polypropylene haptics without anchor loops were treated by exposure to an oxygen plasma for 15 minutes at 80 watts power and a pressure of 0.1 torr. Each group included ten (10) haptics. At various times after completion of the plasma treatment, as indicated below, each of the treated haptics was bonded into a silicone polymer-based optic-like element as described in Example 1. Following such bonding, the haptics were pulled from the optic-like element by a Instron Model 1122 tensile tester and the pull force required to achieve this separation was recorded.

Results of these tests were as follows:

|  | Time from Plasma Treatment to Bonding | Mean Pull Force (gm) |
| --- | --- | --- |
| Group 1 | Immediate | 85.3 ± 41.0 |
| Group 2 | 3 Hours | 106.0 ± 49.4 |
| Group 3 | 8 Hours | 87.2 ± 39.4 |
| Group 4 | 24 Hours | 82.7 ± 37.9 |
| Group 5 | 48 Hours | 64.6 ± 38.3 |
| Group 6 | 7 Days | 13.6 ± 19.7 |

These data indicate the existence of a relationship between the elapsed time from plasma treatment to bonding within the optic in terms of the strength of the haptic-optic bond. The haptic-optic bond is preferably affected within about 48 hours, more preferably within about 24 hours and still more preferably at about three (3) hours, following plasma treatment.

EXAMPLE 6

The lens bonding regions of ten (10) polypropylene haptics without anchor loops were exposed to an oxygen plasma at 80 watts power and a pressure of 0.1 torr for a duration of approximately 30 minutes. Within three (3) hours following plasma treatment, each plasma-exposed lens bonding region was coated by dipping the plasma-exposed lens bonding region into a mixture of the silicone polymer precursor described in Example 1. The coating was allowed to cure. After approximately 24 hours total elapsed time from plasma treatment, the coated region of each of the haptics was molded into a silicone polymer-based optic-like element having the same composition as the coating. Using an Instron Model 1122 tensile tester, the haptics were pulled from the optic-like element and the mean pull force required to achieve this separation was determined to be 104±22 grams.

As a control, ten (10) polypropylene haptics without anchor loops were exposed to an oxygen plasma under the same conditions, and were bonded into silicone polymer-based optic-like element having the same composition within a total elapsed time of 3 hours following plasma treatment. The mean pull force required to achieve separation of the haptics from the optics was 122±34 grams.

These data indicate that the provision of a coating in accordance with the present invention enables a superior strength haptic-optic bond to be formed beyond the time that an equivalent strength bond can be formed using uncoated, plasma-exposed haptics.

While this invention has been described with respect to various specific examples and embodiments, it is to be understood that the invention is not limited thereto and that it can be variously practiced within the scope of the following claims.

What is claimed is:

1. An intraocular lens comprising:
   an optic; and
   at least one haptic including a lens bonding region bonded to said optic, wherein said lens bonding region is exposed to plasma prior to being bonded to said optic, and the bond strength between said haptic and said optic is increased as a result of said exposure relative to a substantially identical intraocular lens including a haptic the lens bonding region of which is not subjected to said exposure.

2. The intraocular lens of claim 1 wherein said haptic comprises a material selected from a group consisting of polypropylene, polymethylmethacrylate, polycarbonates, polyamides, polyimides, polyacrylates, 2-hydroxymethylmethacrylate, poly(vinylidene fluoride), polytetrafluoroethylene, metals and mixtures thereof, and said optic comprises a material selected from the group consisting of silicone polymers, polyacrylates, polyphosphazenes, polyurethanes, hydrogel-forming polymers and mixtures thereof.

3. The intraocular lens of claim 1 wherein said haptic comprises polypropylene, and said optic material comprises a material selected from the group consisting of silicone polymers and mixtures thereof.

4. The intraocular lens of claim 1 wherein said lens bonding region is free of anchor structures designed to mechanically lock said haptic to said optic.

5. The intraocular lens of claim 4 wherein said haptic comprises a material selected from a group consisting of polypropylene, polymethylmethacrylate, polycarbonates, polyamides, polyimides, polyacrylates, 2-hydroxymethylmethacrylate, poly(vinylidene fluoride),- polytetrafluoroethylene, metals and mixtures thereof, and said optic comprises a material selected from the group consisting of silicone polymers, polyacrylates, polyphosphazenes, polyurethanes, hydrogel-forming polymers and mixtures thereof.

6. The intraocular lens of claim 1 wherein said lens bonding region has a substantially uniform cross-section throughout.

7. The intraocular lens of claim 1 wherein said lens bonding region is exposed to said plasma at a sub-atmospheric pressure of at least about 0.01 torr and at an output power in the range of about 30 watts to about 120 watts.

8. An intraocular lens comprising:
   an optic; and
   at least one haptic including a lens bonding region bonded to said optic, wherein said lens bonding region is exposed, prior to being bonded to said optic, to an activated gas plasma formed from a gas selected from the group consisting of oxygen, nitrogen, argon, and mixtures thereof, the bond strength between said haptic and said optic is increased as a result of said exposure relative to a substantially identical intraocular lens including a haptic the lens bonding region of which is not subjected to said exposure.

9. The intraocular lens of claim 8 wherein said haptic comprises polypropylene, said optic comprises a material selected from the group consisting of silicone polymers and mixtures thereof, said lens bonding region is exposed to said activated gas plasma for a period of time in the range of about 1 minute to about 60 minutes, at a pressure in the range of about 0.05 torr to about 0.3 torr and an output pressure in the range of about 5.0 watts to about 100 watts, and said gas is oxygen.

10. The intraocular lens of claim 9 wherein said period of time is in the range of about 15 minutes to about 30 minutes.

11. An intraocular lens comprising:
    an optic; and
    at least one haptic including a lens bonding region the surface of which has been treated by being exposed to a plasma at conditions effective to increase the bond strength between said optic and said haptic relative to a substantially identical intraocular lens including a haptic the lens bonding region of which is not subjected to said exposure.

12. The intraocular lens of claim 11 wherein said haptic includes a coating material located on at least a portion of said lens bonding region.

13. The intraocular lens of claim 12 wherein said lens bonding region is exposed to said plasma prior to being exposed to said coating material.

14. The intraocular lens of claim 12 wherein said coating material comprises a material selected from the group consisting of silicone polymers and mixtures thereof.

15. The intraocular lens of claim 14 wherein said coating material comprises a material selected from the group consisting of silicone polymers and mixtures thereof.

16. The intraocular lens of claim 11 wherein said haptic comprises a material selected from a group consisting of polypropylene, polymethylmethacrylate, polycarbonates, polyamides, polyimides, polyacrylates, 2-hydroxymethylmethacrylate, poly(vinylidene fluoride), polytetrafluoroethylene, metals and mixtures thereof, and said optic comprises a material selected from the group consisting of silicone polymers, polyacrylates, polyphosphazenes, polyurethanes, hydrogel-forming polymers and mixtures thereof.

17. The intraocular lens of claim 11 wherein said optic comprises a material selected from the group consisting of silicone polymers and mixtures thereof.

* * * * *

Adverse Decisions In Interference

Patent No. 5,147,397, F. Richard Christ, David A. Fencil, Patricia M. Knight, INTRAOCULAR LENS AND METHOD FOR MAKING SAME, Interference No. 103,435, final judgment adverse to the patentees rendered June 20, 2000, as to claims 1-17.
*(Official Gazette October 17, 2000)*

Adverse Decision in Interference

Patent No. 5,147,397, F. Richard Christ, David A. Fencil, Patricia M. Knight, INTRAOCULAR LENS AND METHOD FOR MAKING SAME, Interference No. 103,435, final judgment adverse to the patentee rendered June 20, 2000, as to claims 1-17.

*(Official Gazette February 13, 2001)*